US008637269B2

(12) United States Patent
Krebs

(10) Patent No.: US 8,637,269 B2
(45) Date of Patent: Jan. 28, 2014

(54) METHOD FOR THE DETECTION OF MELAMINE

(75) Inventor: Joseph Francis Krebs, Austin, TX (US)

(73) Assignee: Bioo Scientific Corporation, Austin, TX (US)

( * ) Notice: Subject to any disclaimer, the term of this patent is extended or adjusted under 35 U.S.C. 154(b) by 215 days.

(21) Appl. No.: 12/833,580

(22) Filed: Jul. 9, 2010

(65) Prior Publication Data

US 2011/0008809 A1 Jan. 13, 2011

Related U.S. Application Data

(60) Provisional application No. 61/224,692, filed on Jul. 10, 2009.

(51) Int. Cl.
*C12Q 1/34* (2006.01)
(52) U.S. Cl.
USPC .............................................. 435/18; 544/203
(58) Field of Classification Search
USPC ........................................... 435/18; 544/203
See application file for complete search history.

(56) References Cited

U.S. PATENT DOCUMENTS

| 6,315,950 | B1* | 11/2001 | Harp et al. | 422/28 |
| 2009/0221014 | A1* | 9/2009 | Reardon et al. | 435/18 |
| 2011/0294220 | A1* | 12/2011 | Li et al. | 436/23 |

OTHER PUBLICATIONS

Jutzi K. et al. The Degradative Pathway of the s-Triazine Melamine. Biochemistry J 208(3)679-684, 1982.*
Tian Y. et al. Comparison of Three Methods for Detection of Melamine in Compost and Soil. Science of the Total Environment 417-418, 255-262, 2012.*
Seffernick J. et al. Melamine Deaminase and Atrazine Chlorohydrolase. J of Bacteriology 183(8)2405-2410, 2001.*

* cited by examiner

*Primary Examiner* — Ralph Gitomer
(74) *Attorney, Agent, or Firm* — Meyertons, Hood, Kivlin, Kowert & Goetzel, P.C.; Eric B. Meyertons

(57) ABSTRACT

Melamine is a common industrial chemical contaminant which should be absent from food and feed supplies due to melamine's toxicity. Provided is a method to assess the presence of melamine in samples prepared from compositions. The method may include using a microbial enzyme called melamine deaminase which hydrolyzes melamine to ammeline and ammonia. The method may include assessing the presence of any ammonia produced from an enzymatic reaction between the sample and the enzyme.

5 Claims, 1 Drawing Sheet

METHOD FOR THE DETECTION OF MELAMINE

PRIORITY CLAIM

This patent application claims priority to U.S. Provisional Patent Application Ser. No. 61/224,692 entitled "METHOD AND SYSTEM FOR ENZYMATIC DETECTION OF MELAMINE" filed on Jul. 10, 2009, the disclosure of which is hereby incorporated by reference.

BACKGROUND OF THE INVENTION

1. Field of the Invention

The present disclosure generally relates to detection of melamine contaminants in food and feed samples. More particularly, the disclosure generally relates to systems and methods for using a microbial enzyme to hydrolyze melamine to ammeline and ammonia. The produced ammonia is detected and used to assess the presence and amount of melamine in a sample.

2. Description of the Relevant Art

Melamine contamination of food and feed has recently been recognized as a real threat to the global food supply. Melamine is a common industrial chemical with many legitimate commercial uses in the production of hard plastics, tiling, flame retardants, air filters and other products. However it is toxic and should never be added to food. When melamine is ingested it can cause severe kidney damage which is sometimes fatal. Unfortunately, because of its low price, wide availability and high nitrogen content, melamine has been illegally added to food and feed to increase the apparent protein content. This practice is especially common in, for example, baby formula, milk, milk powder and animal feed. Melamine is a very stable substance and when added to raw materials such as milk powder or animal feed it can accumulate in a wide variety of meats and manufactured food items. Melamine has been found in a wide variety of food types, so testing needs have increased recently.

Currently melamine food testing is performed using: 1) immunoassay (ELISA) tests; 2) mass spectrometry; or 3) HPLC. While these proven methods have worked well in the past, they have significant limitations. Mass spectrometry is very expensive and time consuming. Mass spectrometry requires extensive sample preparation procedures, sophisticated instrumentation, and/or highly skilled analysts. In addition, typically each instrument can only test one sample at a time. The same is typically true for HPLC based methods for melamine detection. For reasons of cost and throughput, both mass spectrometry and HPLC are best suited towards very accurate testing of a limited number of samples. In contrast, antibody-based ELISA methods are often a robust and cost-effective alternative to mass spectrometry and HPLC based detection techniques. ELISA techniques are inexpensive and can test multiple samples at once which make them preferable to the other methods for screening applications; especially for large molecular weight analytes. In spite of these qualities ELISA methods have their own set of limitations. ELISA methods typically require multiple incubations and wash steps. Also, as an antibody-based technique, ELISA tests often do not work well to detect low molecular weight analytes like melamine (MW=126). The practical limitations of the currently available techniques severely impede their capacity to monitor the immense volume and variety of food samples currently under scrutiny. It would be highly desirable to develop a method for melamine detection which does not suffer from these limitations.

SUMMARY

This disclosure describes an enzyme-based method to detect melamine. The assay uses an enzyme called melamine deaminase which is used by specific bacteria to degrade to melamine to ammeline and ammonia. The ammonia formed from the melamine can then be detected using ammonia detection methods (e.g., colorimetric detection using the Berthelot reaction). This method can be used for the rapid and specific detection of melamine contaminants in food and/or feed samples.

Many food samples can contain ammonia and other agents which interfere with the enzyme-based melamine detection method. In some embodiments, the method may include a sample preparation procedure to remove ammonia and/or interfering substances from samples prior to the enzymatic reaction to detect melamine. This procedure may utilize a cation exchange, solid phase extraction procedure for sample clean-up. This procedure removes ammonia and/or other potentially-interfering impurities from the samples while retaining the melamine in the samples in an aqueous matrix compatible with optimal melamine deaminase activity.

When the sample preparation procedure (to purify melamine from matrix impurities) is used to prepare samples for the melamine deaminase enzyme reaction, the method may be used to enzymatically convert melamine from the samples to ammonia. The ammonia emanating from the food sample may be detected using ammonia detection methods (e.g., the colorimetric Berthelot (indophenol) reaction). Therefore, colorimetric detection of melamine present in food samples can be achieved by sequentially linking the sample preparation procedure, the enzymatic assay and the ammonia detection assay. In some embodiments, these three individual components may be combined to create a test kit for the detection of melamine in food samples. For example, cation exchange SPE columns can be used to prepare milk food samples for enzymatic degradation of melamine in test reactions in 96 well microplates. Since the amount of ammonia present in the wells is proportional to the amount of melamine present in the original sample, subsequent addition of ammonia-reactive chromogenic reagents to the microplate causes a color change proportional to the level of melamine in the sample. Using this strategy, our method may be used to create colorimetric microplate-based test kits to detect and quantify melamine in food samples such as milk. Using this basic strategy, one skilled in the relevant art could also create alternate versions of test kits which use alternative methods to produce purified samples compatible with the enzyme-based melamine conversion and alternate methods for detection of ammonia product.

BRIEF DESCRIPTION OF THE DRAWINGS

Advantages of the present invention may become apparent to those skilled in the art with the benefit of the following detailed description of the preferred embodiments and upon reference to the accompanying drawings.

Figure 1:
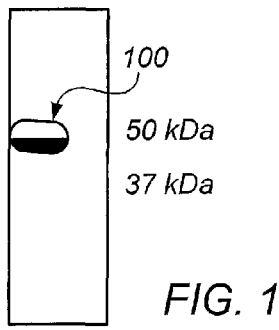
FIG. 1 depicts a graphical representation of a Coomassie-stained SDS-PAGE gel of purified $His_6$-tagged melamine deaminase (Tri A) enzyme. The molecular weights of the size markers (in kDa) is indicated to the right of the gel. The purified stained enzyme is indicated by arrowhead 100.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION

It is to be understood the present invention is not limited to particular devices or biological systems, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Thus, for example, reference to "a linker" includes one or more linkers.

Definitions

Unless defined otherwise, all technical and scientific terms used herein have the same meaning as commonly understood by one of ordinary skill in the art.

The term "food matrices" as used herein generally refers to any substance which humans eat or otherwise ingest or take in to their body. In some embodiments, this may include any substance which is consumed by a nonhuman first but is ultimately consumed by a human due to the human's consumption of the nonhuman entity or a second nonhuman entity which consumed the nonhuman entity.

The term "feed matrices" as used herein generally refers to any substance which nonhumans eat or otherwise ingest or take in to their body.

The term "interfering agents" as used herein generally refers to any substance which may interfere with a reaction (e.g., an enzymatic reaction) and/or detection of a particular substance (e.g., ammonia).

Microbes are capable of specifically transforming a tremendous array of diverse organic chemical substrates. Transforming microbes are sometimes used for bioremediation purposes to remove toxic substances, such as spilled oil, from the environment. Melamine can be found in the environment, so a number of bacteria have been isolated from the environment which can specifically utilize melamine as a carbon source for growth. These bacteria transform melamine by successively removing the amino groups from melamine to form cyanuric acid, which is then degraded as an energy source. The biochemical pathways in these microbes contain specialized enzymes which specifically process melamine and its metabolites in a serial manner.

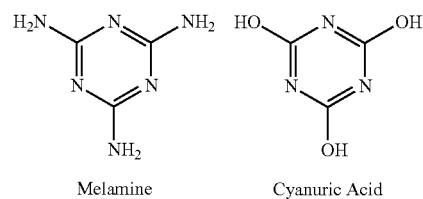 [SMILES: Nc1nc(N)nc(N)n1 ; Oc1nc(O)nc(O)n1]

Melamine          Cyanuric Acid

One bacterial strain capable of using melamine as a carbon source for growth is *Pseudomonas* sp. strain NRRL B-12227. This species can convert melamine to cyanuric acid using a pathway containing sequential deaminating enzymes. The first enzyme in this pathway (Tui A) has been cloned and expressed in recombinant form. This metalloenzyme catalyzes the hydrolytic deamidation of melamine to ammeline (and also, to a lesser extent, converts ammeline to ammelide). In addition to ammeline, deamination of melamine by the Tri A enzyme also produces ammonia.

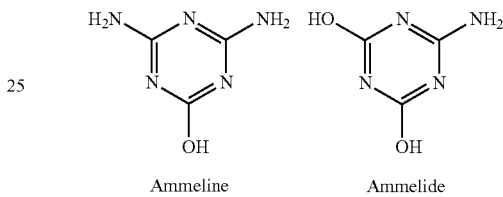

Ammeline          Ammelide

In some embodiments, a method may include using an enzyme to detect melamine in compositions. Enzymes may include melamine deaminase (MDA). Compositions may include crude food matrices (e.g., milk, powdered milk, cream, ice cream, chocolate drink, seafood, meat) and/or pharmaceutical ingredients. MDA enzyme can be produced recombinantly in bacterial cultures. Upon isolation, MDA enzyme may be stable when frozen or refrigerated after dilution with an equal volume of glycerol. When diluted into aqueous solutions containing melamine, MDA enzyme may hydrolyze melamine. MDA enzyme may hydrolyze melamine to form ammeline and ammonia products.

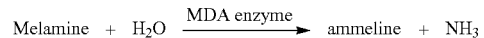

Melamine + $H_2O$ $\xrightarrow{\text{MDA enzyme}}$ ammeline + $NH_3$

The enzymatic hydrolysis of melamine may proceed rapidly at room temperature in aqueous buffered solutions (pH ~8). In some embodiments, an amount of ammonia product produced during the enzymatic reaction may be proportional to the amount of melamine originally present in the sample.

The ammonia produced from the melamine may be readily detected by a number of methods. In some embodiments, ammonia may be detected using the Berthelot reaction which uses salicylic acid in the presence of alkaline sodium hypochlorite to form colored indophenol product.

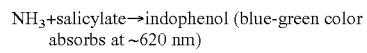

$NH_3$+salicylate→indophenol (blue-green color absorbs at ~620 nm)

The amount of melamine originally present in the sample can be measured by detecting the ammonia product using a number of different detection methods. In some embodiments, ammonia may be detected using colorimetric indophenol production. In some embodiments, ammonia may be detected using NAD+ production using glutamate dehydrogenase (coupled enzymatic assay). In some embodiments, ammonia may be detected using an ammonia-specific electrode. Progress of the enzymatic reaction may be detected using a number of methods. In some embodiments, progress of the enzymatic reaction may be detected fluorometrically (e.g., using o-phthaldialdehyde). In some embodiments, progress of the enzymatic reaction may be detected by measuring the change in solution pH associated with product formation or using a pH-stat method. A practitioner skilled in the art could detect the ammonia product using a number of other ammonia detection techniques.

It is important to note that ammonia is sometimes present in food and feed samples. For example, milk can contain significant levels of ammonia (>1 ppm). Therefore, detection of low quantities of ammonia produced by the enzyme in milk and other food matrices is nontrivial. Food matrices may contain agents which can interfere with ammonia detection (e.g., glycine). Therefore, it would be highly desirable to develop a method for preparing a sample.

In some embodiments, a method may include preparing a sample to remove endogenous ammonia and/or interfering agents (e.g., substances which may interfere with the enzymatic reaction and/or detection of the ammonia). A sample may be prepared prior to the enzyme reaction to detect melamine is conducted. In some embodiments, sample preparation may include solid-phase extraction (SPE). SPE may be conducted using a cation exchange resin (e.g., Strata X-C). While cation exchange SPE based sample preparation methods are currently used for preparation of samples for melamine analysis by mass spectrometry, current methods utilize high levels of ammonia to elute the melamine from the SPE column. Since ammonia-based methods such as these are not compatible with our enzyme based-detection scheme (since ammonia would increase the background signal and potentially inhibit the enzyme) the elution step of the SPE scheme described herein does not employ ammonia. In some embodiments, a sample preparation method may include using a solution containing Na-MOPS buffer in methanol for the elution step.

While the modified SPE sample prep method works well to prepare samples for enzyme-based melamine detection, other sample preparation methods such as heating the milk to volatilize the ammonia (at elevated pH) or using amine-specific chemical agents to modify the ammonia may be useful for sample preparation.

In some embodiments, a method for detecting melamine may include:
preparing a sample (e.g., remove ammonia, remove interfering substances);
mixing the sample with enzyme (e.g., in a buffer aqueous solution, Sample+MDA enzyme→NH$_3$); and
detecting an ammonia product (e.g., colorimetrically using the Berthelot reaction,

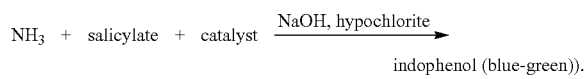

indophenol (blue-green)).

In some embodiments, a melamine-dependent color change may be observed spectrophotometrically (e.g., in a cuvette, in a flow-cell, or in a microplate used for ELISA assays). As mentioned, a number of other useful detection methods for ammonia detection such as detection with an ammonia-specific electrode or paper dipstick may be employed.

EXAMPLES

Having now described the invention, the same will be more readily understood through reference to the following example(s), which are provided by way of illustration, and are not intended to be limiting of the present invention.

Example 1

Expression and Purification of Recombinant Melamine Deaminase Enzyme

The TriA gene encoding the melamine deaminase enzyme was inserted into the multiple cloning site region of the pET 24b bacterial expression plasmid. This subcloning strategy places the gene under the transcriptional regulation of the T7 RNA polymerase and fuses a His$_6$ peptide tag onto the C-terminus of the protein to facilitate purification. We expressed the protein (MW about 50 kDa) in *E. coli* strain BL21 (DE3) and obtained significant amounts of soluble protein in the induced bacterial cultures. After disruption the lysed cell extract was passed over a Talon Cobalt column to bind the His$_6$-tagged protein. After washing the column the bound protein was eluted from the column and dialyzed to remove imidazole. SDS-PAGE analysis indicates that the isolated recombinant protein is highly pure (FIG. 1).

Example 2

Enzymatic Detection of Melamine in Microtiter Plates

Figure 2:
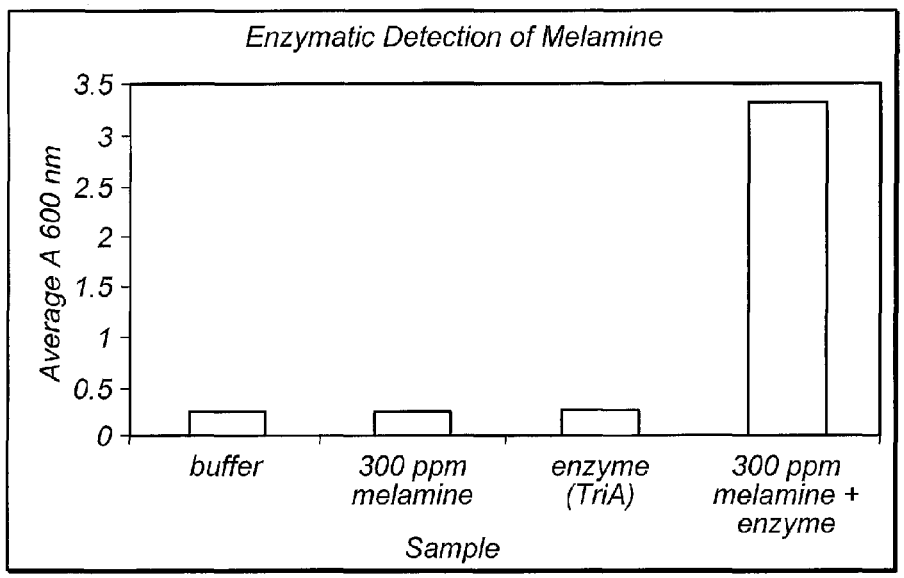
FIG. 2 depicts a graphical representation of the results of an enzyme-based, colorimetric detection of melamine in samples measured in a 96 well microplate. Using indophenol-based colorimetric detection, ammonia produced from the enzyme-mediated degradation of melamine produces a strong absorbance at a wavelength of 600 nm.

Purified, desalted recombinant MDA enzyme (about 2 mg/ml in 0.1 M Na-MOPS buffer pH 7) and melamine (1000 ppm) were diluted into 0.1 M Na-MOPS buffer (pH 7) and incubated overnight (about 12 hours) at room temperature. Reaction aliquots were removed and tested for the production of ammonia by mixing the samples with salicylate/nitroprusside and NaOH/hypochlorite reagents in 96 well microtiter plates. When melamine and enzyme are both present in the wells, a strong color change was observed (FIG. 2), indicating the MDA-mediated conversion of melamine to ammonia in these samples. The observed color change requires the presence of both melamine and MDA enzyme; no color change was observed in wells from samples from control reactions containing only melamine or enzyme alone, indicating that no ammonia is present in these samples.

Example 3

Removal of Endogenous Ammonia from Samples

Figure 3:
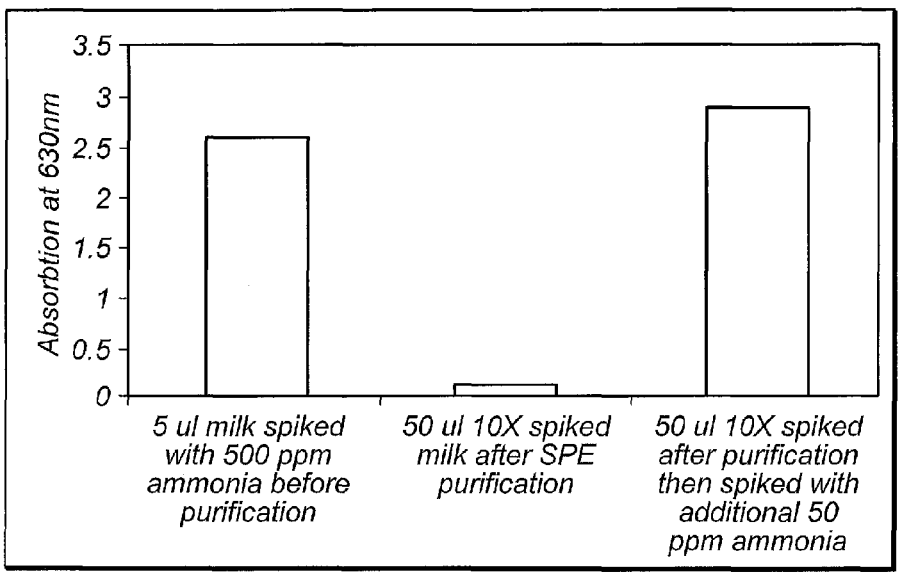
FIG. 3 depicts a graphical representation of the results of the removal of ammonia from milk samples using solid-phase extraction based process.

A 15 ml portion of reconstituted powdered milk was spiked with 5 ppm ammonia (as ammonium chloride). 0.075 ml glacial acetic acid and 10 ml acetonitrile were added to the milk and after mixing, the samples were centrifuged for 10 min at 4,000×g. The supernatants were loaded onto 100 mg Strata X-C cation exchange SPE columns (conditioned with 2 ml methanol and 2 ml 40% acetonitrile/0.5% acetic acid). The columns were then washed with 2 ml 40% acetonitrile/0.5% acetic acid, then 2 ml 0.5% acetic acid and then with 2 ml methanol. The samples were eluted from the column with 1 ml methanol containing 0.09 g/ml Na-MOPS plus 0.0009 g/ml MOPS and then 1 ml methanol. After drying off the methanol, the samples were dissolved in 1.5 ml deionized water (approximately 10× concentration of the original 15 ml milk sample). Samples were mixed with salicylate/nitroprusside and NaOH/hypochlorite reagents in microtiter plates to detect ammonia present in samples (using the Bethelot reaction to convert ammonia to colored indophenol). Strong color changes were observed in unpurified milk samples spiked with ammonia or samples spiked with ammonia after purification, but no detectable color change was observed in spike samples after purification indicating that our procedure efficiently removes ammonia from the samples (FIG. 3). Although ammonia is removed from samples, melamine is efficiently purified using this procedure.

Example 4

Detection of Melamine in Milk Samples

A 15 ml portion of reconstituted powdered milk is spiked with 0.03 ml of 1000 ppm melamine in water (final melamine concentration of 2 ppm). A 15 ml portion of unspiked milk may be tested as a negative control. 0.075 ml glacial acetic acid and 15 ml acetonitrile is added to each of the milk samples and after mixing, the samples are centrifuged for 10 min at 4,000×g. The supernatants are loaded onto 60 mg Strata X-C cation exchange SPE columns (conditioned with 2 ml methanol and 2 ml 50% acetonitrile/0.5% acetic acid). The columns are washed with 2 ml 50% acetonitrile/0.5% acetic acid, then 2 ml 0.5% acetic acid and then with 2 ml methanol. The samples are eluted from the column with 0.6 ml methanol containing 0.09 g/ml Na-MOPS plus 0.0009 g/ml MOPS and then 0.6 ml methanol. After drying off the methanol, the samples are dissolved in 0.6 ml deionized water. 0.2 ml of the samples are transferred to polystyrene 96 well microplate wells and 0.02 ml of melamine deaminase enzyme (about 10 micrograms of enzyme) is added to each well and after mixing, the samples are incubated at room temperature for 10-15 minutes. Ammonia derived from the melamine is then detected by adding salicylate/nitroprusside and NaOH/hypochlorite reagents into microtiter plate wells. The resulting color change of the samples containing melamine is then detected using a plate reader (absorbance of light near 630 nm wavelength).

Example 5

An Enzyme-Based Kit to Detect Melamine in Food Samples

Melamine in food or feed samples may be determined using a test kit which contains a solid-phase extraction cartridge, a melamine deaminase enzyme reagent, a buffer used to dilute the enzyme, reagents to detect ammonia produced from melamine analyte, melamine reference standards (to verify test kit performance) and a polystyrene 96 well plate. After preparing the samples for analysis according to the instruction manual, the samples (or reference standards) are mixed with enzyme in 96 well plate wells and incubated to convert melamine to ammonia. After incubation, ammonia detection reagents (salicylate/nitroprusside and NaOH/hypochlorite) are mixed with the samples and allowed to incubate for 5 min to produce colored indophenol in the wells. The absorbance of each of the samples is measured at a wavelength of about 620 nm and compared to the absorbance of the wells containing known amounts of melamine standards. The following articles are incorporated by reference as if fully set forth herein:

U.S. Pat. No. 6,825,001 to Wackett, Lawrence P., Sadowsky, Michael J., de Souza, Mervyn L., and Minshull, Jeremy S. DNA molecules and protein displaying improved triazine compound degrading ability;

U.S. Pat. No. 6,284,522 to Wackett, Lawrence P., Sadowsky, Michael J., and de Souza, Mervyn, L. Isolated and purified DNA molecule and protein for the degradation of triazine compounds;

U.S. Pat. No. 6,265,201 to Wackett, Lawrence P., Sadowsky, Michael J., de Souza, Mervyn L., and Minshull, Jeremy S. DNA molecules and protein displaying improved triazine compound degrading ability;

Andersen W C, Turnipseed S B, Karbiwnyk C M, Clark S B, Madson M R, Gieseker C M, Miller R A, Rummel N G, Reimschuessel R. (2008) Determination and confirmation of melamine residues in catfish, trout, tilapia, salmon, and shrimp by liquid chromatography with tandem mass spectrometry. J Agric Food Chem. 56:4340-7;

de Souza M L, Wackett L P, Boundy-Mills K L, Mandelbaum R T, Sadowsky M J. (1995) Cloning, characterization, and expression of a gene region from *Pseudomonas* sp. strain ADP involved in the dechlorination of atrazine. Appl Environ Microbiol. 61:3373-8;

Heller D N, Nochetto C B. Simultaneous determination and confirmation of melamine and cyanuric acid in animal feed by zwitterionic hydrophilic interaction chromatography and tandem mass spectrometry. (2008) Rapid Commun Mass Spectrom. 22:3624-32;

Ishiwata H, Inoue T, Yamazaki T, Yoshihira K. (1987) Liquid chromatographic determination of melamine in beverages. J Assoc Off Anal Chem. 70: 457-60;

Jutzi K, Cook A M, Hater R. (1982) The degradative pathway of the s-triazine melamine.
The steps to ring cleavage. Biochem J. 208: 679-84;

Kim B, Perkins L B, Bushway R J, Nesbit S, Fan T, Sheridan R, Greene V. (2008)
Determination of melamine in pet food by enzyme immunoassay, high-performance liquid chromatography with diode array detection, and ultra-performance liquid chromatography with tandem mass spectrometry. J AOAC Int. 91: 408-13;

Mulbry W W (1994) Purification and Characterization of an Inducible s-Triazine Hydrolase from *Rhodococcus corallinus* NRRL B-15444R. Appl Environ Microbiol. 60: 613-8;

Neeley W E, Phillipson J. (1988) Automated enzymatic method for determining ammonia in plasma, with 14-day reagent stability. Clin Chem. 34: 1868-9;

Seffernick J L, de Souza M L, Sadowsky M J, Wackett L P. (2001) Melamine deaminase and atrazine chlorohydrolase: 98 percent identical but functionally different. J. Bacteriol. 183: 2405-10;

Tsuboi T, Hirano Y, Shibata Y, Motomizu S. (2002) Sensitivity improvement of ammonia determination based on flow-injection indophenol spectrophotometry with manganese(II) ion as a catalyst and analysis of exhaust gas of thermal power plant. Anal Sci 18: 1141-4; and Yokley R A, Mayer L C, Rezaaiyan R, Manuli M E, Cheung M W. (2000) Analytical method for the determination of cyromazine and melamine residues in soil using LC-UV and GC-MSD. J Agric Food Chem. 48: 3352-8.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S.

patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method of quantitatively determining melamine in a composition comprising:
   providing a sample of the composition;
   extracting ammonia from the sample to form an extracted sample;
   forming a solution of the extracted sample, wherein the solution comprises melamine present in the sample;
   adding a solution of melamine deaminase and salicylate to the solution of the extracted sample;
   determining an amount of indophenol produced;
   correlating the amount of indophenol produced to an amount of ammonia produced by the enzymatic reaction of melamine deaminase with melamine present in the solution of the extracted sample; and
   correlating the amount of ammonia produced to an amount and/or a relative amount of melamine in the composition.

2. The method of claim 1, further comprising detecting ammeline produced by the enzymatic reaction.

3. The method of claim 1, wherein extracting ammonia from the sample comprises using solid-phase extraction on the sample using an eluent comprising a Na-MOPS buffer.

4. The method of claim 1, wherein extracting ammonia from the sample comprises using solid-phase extraction with a cation exchange resin.

5. The method of claim 1, wherein the composition is derived from a food, a feed and/or an environmental source.

* * * * *